United States Patent [19]
Askill et al.

[11] Patent Number: 5,957,877
[45] Date of Patent: *Sep. 28, 1999

[54] METHODS FOR DRAPING SURGICAL SITES USING PERIPHERAL CYANOACRYLATE DRAPES

[75] Inventors: Ian N. Askill; Michael M. Byram, both of Colorado Springs, Colo.; Richard J. Greff, St. Pete Beach, Fla.; Richard T. Vanryne, Lake Forest, Calif.

[73] Assignee: MedLogic Global Corporation, Colorado Springs, Colo.

[ * ] Notice: This patent is subject to a terminal disclaimer.

[21] Appl. No.: 08/963,370

[22] Filed: Nov. 3, 1997

[51] Int. Cl.$^6$ ........................................................ A61F 13/00
[52] U.S. Cl. ................................ 602/54; 602/42; 602/43; 602/50; 514/527; 524/776; 128/849
[58] Field of Search .............................. 128/849; 602/42, 602/43, 50, 54; 514/527; 524/776

[56] References Cited

U.S. PATENT DOCUMENTS

| | | |
|---|---|---|
| 3,654,239 | 4/1972 | McIntire et al. . |
| 3,722,599 | 3/1973 | Robertson . |
| 4,038,345 | 7/1977 | O'Sullivan et al. . |
| 5,254,132 | 10/1993 | Barley et al. . |
| 5,306,490 | 4/1994 | Barley . |
| 5,328,687 | 7/1994 | Leung . |
| 5,480,935 | 1/1996 | Greff et al. . |
| 5,653,769 | 8/1997 | Barley et al. . |
| 5,684,042 | 11/1997 | Greff et al. . |
| 5,730,994 | 3/1998 | Askill et al. . |

FOREIGN PATENT DOCUMENTS

WO 93/25196  12/1993  WIPO .

OTHER PUBLICATIONS

Masterson, M.D., "Skin Preparation", Chapter 9, in *Surgical Infections, Diagnosis and Treatment*, Meakins Ed., Scientific American, Inc., New York, USA, Publisher, pp. 119–125 (1994).

Osuna, et al., "Comparison of an Antimicrobial Adhesive Drape and Povidone–Iodine Preoperative Skin Preparation in Dogs", Veterinary Surgery, 21(6):458–462 (1992).

Hagen, et al., "A Comparison of Two Skin Preps Used in Cardiac Surgical Procedures", AORN Journal, 62(3):393–402 (1995).

Alexander, et al., "Development of a Safe and Effective One–Minute Preoperative Skin Preparation", Arch. Surg., 120:1357–1361 (1985).

Chiu, et al., "Plastic Adhesive Drapes and Wound Infection After Hip Fracture Surgery", Aust. N.Z. J. Surg., 63:798–801 (1993).

Ritter, et al., "Retrospective Evaluation of an Iodophor–Incorporated Antimicrobial Plastic Adhesive Wound Drape", Clinical Orthopedics and Related Research, pp. 307–308 (1988).

Duhaime, et al., "Distribution of Bacteria in the Operating Room Environment and its Relation to Ventricular Shunt Infections: a Prospective Study", Child's Verv. Syst., 7:211–214 (1991).

Blum, et al., In vitro Determination of the Antimicrobial Properties of Two Cyanoacrylate Preparations, J. Dent. Res., 54(3):500–503 (1975).

*Primary Examiner*—John G. Weiss
*Assistant Examiner*—Kelvin Hart
*Attorney, Agent, or Firm*—Burns Doane Swecker & Mathis, LLP

[57] ABSTRACT

Disclosed are methods for draping a surgical site prior to surgery. Specifically, the methods of this invention involve the in situ formation of a cyanoacrylate polymeric drape on the skin surface of a patient peripheral to the surgical site. Surgery is then conducted at the surgical site.

16 Claims, No Drawings

METHODS FOR DRAPING SURGICAL SITES USING PERIPHERAL CYANOACRYLATE DRAPES

BACKGROUND OF THE INVENTION

Field of the Invention

This invention is directed to methods for draping a surgical site prior to surgery. Specifically, the methods of this invention involve the in situ formation of a polymeric cyanoacrylate drape over mammalian skin surfaces peripheral to and surrounding the intended surgical site. Surgery is then conducted through the intended surgical site.

References

The following publications, patent applications and patents are cited in this application as superscript numbers:

1. Masterson, M. D., "Skin Preparation", Chapter 9, in *Surgical Infections, Diagnosis and Treatment*, Meakins, Ed., Scientific American, Inc., New York, USA, Publisher, pp. 119–125 (1994)
2. Osuna, et al., "*Comparison of an Antimicrobial Adhesive Drape and Povidone-Iodine Preoperative Skin Preparation in Dogs*", Veterinary Surgery, 21(6):458–462 (1992)
3. Hagen, et al., "*A Comparison of Two Skin Preps Used in Cardiac Surgical Procedures*", AORN Journal, 62(3):393–402 (1995)
4. Alexander, et al., "*Development of a Safe and Effective One-Minute Preoperative Skin Preparation*", Arch. Surg., 120:1357–1361 (1985)
5. Chiu, et al., "*Plastic Adhesive Drapes and Wound Infection After Hip Fracture Surgery*", Aust. N.Z. J. Surg., 63:798–801 (1993)
6. Barley, "*Methods for Retarding Blister Formation by Use of Cyanoacrylate Adhesives*", U.S. Pat. No. 5,306,490, issued Apr. 26, 1994
7. Barley, et al., *Methods for Treating Suturable Wounds by Use of Sutures and Cyanoacrylate Adhesives*, U.S. Pat. No. 5,254,132, issued Oct. 19, 1993
8. McIntire, et al., U.S. Pat. No. 3,654,239, for *Process for the Preparation of Poly(α-Cyanoacrylates)*, issued Apr. 4, 1972
9. Barley, et al., International Patent Application Publication No. WO 93/25196, for *Methods for Treating Non-Suturable Wounds by Use of Cyanoacrylate Adhesives*, published Dec. 23, 1993
10. Barley, et al., U.S. Pat. No. 5,653,789, for *Methods for Reducing Skin Irritation From Artificial Devices by Use of Cyanoacrylate Adhesives*, issued Aug. 5, 1997
11. Ritter, et al., "*Retrospective Evaluation of an Iodophor-Incorporated Antimicrobial Plastic Adhesive Wound Drape*", Clinical Orthopedics and Related Research, pp. 307–308 (1988)
12. Duhaime, et al., "*Distribution of Bacteria in the Operating Room Environment and its Relation to Ventricular Shunt Infections: a Prospective Study*", Child's Verv. Syst., 7:211–214 (1991)
13. O'Sullivan, et al., U.S. Pat. No. 4,038,345, for *High Viscosity Cyanoacrylate Adhesive Compositions, and Process for Their Preparation*, issued Jul. 26, 1977
14. Robertson, U.S. Pat. No. 3,722,599 for *Fluorocyanoacrylates* issued Mar. 27, 1973
15. Leung, U.S. Pat. No. 5,328,687 for *Biocompatible Monomer and Polymer Compositions*, issued Jul. 12, 1994
16. Askill, et al., U.S. patent application Ser. No. 08/781,279, for *Methods for Draping Surgical Incision Sites* filed Jan. 10, 1997
17. Askill, et al., U.S. patent application Ser. No. 08/912,678, for *Methods for Draping Surgical Incision Sites* filed Aug. 18, 1997
18. Greff et al., U.S. Pat. No. 5,480,935, for *Cyanoacrylate Adhesive Compositions* issued on Jan. 2, 1996
19. Greff, et al., U.S. Pat. No. 5,684,042 for *Cyanoacrylate Compositions Comprising an Antimicrobial Agent* to issue Nov. 4, 1997
20. Blum, et al., *In vitro Determination of the Antimicrobial Properties of Two Cyanoacrylate Preparations*, J. Dent. Res., 54(3):500–503 (1975)

All of the above publications, patent applications and patents are herein incorporated by reference in their entirety to the same extent as if each individual publication, patent application or patent was specifically and individually indicated to be incorporated by reference in its entirety.

State of the Art

Reducing morbidity and/or infection associated with surgical procedures necessitates the thorough preparation of the patient's skin prior to initiating any incision into the skin as part of the surgical procedure. The primary reason for patient skin preparation is to reduce the risk of wound infection by introduction of microbes into the incision site[1] from either the skin or from the air.[12] In turn, reduction in such risk correlates, obviously, with reductions in the population of microbes on the skin surface and especially at the skin surface adjacent to the incision site.

Suitable skin preparation involves, for example, application of an antimicrobial agent onto and around the skin surface adjacent to the incision site which reduces the population of microbes on these surfaces and, hence the relative risk of infection. However, the skin is never completely sterilized during these procedures and microbes from hair follicles and sweat/sebaceous glands will migrate to the surface of the skin thereby raising microbial populations and accordingly relative infection risks.[2] To counter possible microbial migration into the incision, it has become common practice to employ a surgical incise drape, where practicable, over the patient's incision site.

Conventional surgical incise drapes include those which comprise preformed, sized polymeric films coated with a pressure-sensitive adhesive. In some cases, an antimicrobial agent is incorporated directly into the adhesive in order to permit a continuous release of the antimicrobial agent onto the skin.[3,11] After application of an antimicrobial agent onto the skin surface of the patient, the surgical incise drape is applied, adhesive side down, with pressure to effect adherence of the drape to the skin. A surgical incision is then made through the drape and the requisite surgery is conducted through this incision. After completion of the surgery, the drape is conventionally removed from the skin surface prior to final incision closure.

A fenestrated drape is a drape cut to form a window or opening. This opening or window is placed over the surgical site or wound.

Notwithstanding the benefits associated with a surgical incise drape, several problems exist which have both limited the general applicability of these drapes to all surgical incisions and have actually increased the relative risk of infection. Specifically, the first most common and potentially serious problem associated with the use of conventional surgical incise drapes is the separation or lifting of the drape from the skin surface during surgery. In one study, it was reported that up to 44% of the drapes experienced at least partial separation during human surgery[2]. In turn, Alexander, et al.[4] report a sixfold increase in infection rates in operations in which the surgical incise drape separated from the skin during surgery as compared to infection rates in which the drape did not separate from the skin. Without being limited by any theory, it is generally believed that occlusion of the skin by the surgical incise drape provides a moist, warm skin surface which encourages microbial growth. It is further believed that separation of the drape from the skin during surgery permits migration of microbes and/or microbial growth at these sites and, accordingly, in such cases, the use of a drape can actually promote rather than retard microbial populations at the incision site.

Non-adherence of the surgical incise drape to the patient's skin is, of course, related to adhesive failure as well as wrinkling of the preformed polymeric film during application. In the former case, this has lead to some attempts to increase the amount and/or strength of adhesive employed in the drape to secure the drape to the mammalian skin surface. However, this in turn may lead to more rather than fewer complications. In particular, since the drape is conventionally removed from the skin shortly after surgery by, e.g., the peeling or pulling off of the drape, an increase in the relative strength of the adhesive leads to increased difficulty in removing the drape from the skin. The effort required to effect removal can also lead to skin tearing and irritation, especially adjacent to the incision site, as well as removal of hair. Skin tearing is clearly disadvantageous and invariably raises additional infection risks because the mammalian skin surface is open (compromised) and therefore susceptible to infection. Moreover, the removal of hair (shaving) has also been associated with increased infection rates[2] and hair removal due to adhesive/drape removal from the mammalian skin can also be expected to provide similar increased infection rates.

In the latter case, wrinkling of the polymeric drape is essentially irreversible because the wrinkles cannot be smoothed out absent complete removal of the drape and drapes, once removed, typically cannot be reapplied to the skin. Additionally, air pockets found in the wrinkles are undesirable because they provide a source of microbes adjacent to the skin and, in some cases, promote microbial growth. Wrinkling of the polymeric film is common to most applications of the surgical incise drapes but is particularly problematic with contoured surfaces such as elbows, knees, bony hips, etc. This, in turn, has limited the use of such conventional drapes.

An additional problem associated with preformed polymeric films used as surgical incision drapes arises because such drapes do not conform well to three dimensional contours of the human body thereby increasing the likelihood of separation during surgery. For example, while abdominal surfaces through which the surgical incision is to be made are typically good candidates for conventional surgical incise drapes, other surfaces such as elbow, knee, foot, and bony hip surfaces (as examples) have three dimensional contours which render consistent adherence of the drape over the incision site during surgery problematic at best. In this regard, Chiu, et al.[5] report that the use of sterile adhesive drapes during hip fracture surgeries appeared to have actually encouraged microbial accumulation in the skin adjacent to the wound.

Still a further problem arises from the fact that many adhesives employed with preformed polymeric films do not adhere well to hair thereby limiting their utility[2]. Additionally, as noted above, shaving to remove hair prior to surgery has been clinically associated with increased wound infection In an alternative embodiment, the art has proposed formation of surgical incise drapes by the use of emulsions/solutions containing a volatile organic solvent and a polymer. Upon application to the skin, the solvent dissipates leaving a polymeric film which acts as the incise drape. Significant problems exist with such a procedure and, in particular, the polymeric film lacks strong adhesion to the skin and the volatile solvent can create irritation (e.g., skin, nose, etc.) as well as can be the source of a fire hazard in the operating room.

While the most important purpose of using surgical incise drapes is to prevent postoperative wound infections, the simple fact of the matter is that the drapes of the prior art are removed after surgery and there is, accordingly, no postoperative antimicrobial effect available to the skin surface at or near the surgical incision site.

Lastly, the surgical incise drape cannot be applied during surgery to repair a wound, such as a puncture wound. The conventional surgical incise drape must be applied to intact skin prior to incision. It cannot be applied to open wounds or where objects have punctured the skin (i.e. compound bone fractures and foreign object punctures).

An alternated to conventional surgical drapes is the formation of a cyanoacrylate polymeric drape, as described in U.S. patent application Ser. Nos. 08/912,678 and 08/781,279[16,17], over the intended surgical incision site prior to surgery. Notwithstanding the benefits associated with the formation of a cyanoacrylate polymeric drape over the intended surgical incision site, which benefits are set forth in U.S. patent application Ser. Nos. 08/912,678 and 08/781,279[16,17], there are several situations in which this type of drape may be problematic. For example, when the surgical site is a large or irregular wound, for example, a tear of the skin. In such situations, it may not be possible to apply cyanoacrylate prepolymer to the incision site without penetration of the prepolymer from the surface of the epidermis to or beyond the dermal layer and subsequent polymerization. Robertson[14] and Leung[15] report that the polymerization of cyanoacrylates in vivo and inclusion of the resulting polymer into the patient's body can result in a reaction by the patient resulting in inflammation of the tissues. Such inflammation at the site of injury would be disadvantageous.

Secondly, it may prove disadvantageous to form a cyanoacrylate polymeric drape over areas of moisture such a mucous membranes. Such areas are problematic for cyanoacrylate drapes because the polymer can polymerize in the presence of moisture and if care is not taken the polymerization of the cyanoacrylate will bind the mucous membranes together or the heat generated by the polymerization of the cyanoacrylate composition in the presence of moisture may damage fragile tissue structures.

Finally, it may prove undesirable to form a cyanoacrylate polymeric drape over an intended surgical incision site prior to surgery if the cyanoacrylate polymeric drape masks or obscures the intended incision site. Specifically, if the cyanoacrylate polymeric drape contains an opaque or colored material, the polymerization of the colored cyanoacrylate polymeric drape over the intended incision site may obscure the intended site, impeding or preventing the surgeon from making a precise incision.

This invention is directed, in part, to the discovery that the in situ formation of a cyanoacrylate polymeric drape peripheral to the surgical site prior to surgery overcomes many of the prior art problems associated with the use of conventional surgical incise drapes and is complementary to the methods of U.S. Ser. Nos. 08/781,279 and 08/912,678[16,17].

The cyanoacrylate polymer is known to have bacteriostatic properties[20] and the cyanoacrylate monomer permits the inclusion of compatible antimicrobial agents if such is desired. Still another advantage is the formation of an appropriately configured drape without the need to modify the dimensions provided with commercial polymeric drapes. Still further, the methods of this invention result in incise drapes which mold directly to the multiple contours adjacent to the intended surgical site.

In addition, formation of the cyanoacrylate polymeric drape peripheral to the surgical site provides additional advantages not achieved by application of the cyanoacrylate polymeric drape directly to the intended surgical site. The formation of a peripheral drape allows an unobscured view of the incision site. Furthermore, in the repair of gaping wounds or puncture wounds, the formation of a peripheral drape provides bactericidal and antimicrobial benefits adjacent such wounds.

The use of cyanoacrylate polymers per this invention is in contrast to their known medical uses as an alternative or adjunct to sutures[7] or as a hemostat[8]. Other described uses of cyanoacrylate polymers include their use to prevent friction blister formation[6], treat small non-suturable wounds[9], and inhibit surface skin irritation arising from friction between the skin surface and artificial devices such as tapes, prosthetic devices, casts, and the like.[10]

SUMMARY OF THE INVENTION

This invention is directed to methods for draping a surgical site by the in situ formation of a polymeric cyanoacrylate drape over the mammalian skin surface peripheral to and surrounding the intended surgical site.

An situ polymerization of the cyanoacrylate composition provides for an adherent polymeric film peripheral to the surgical site which acts as a surgical incise drape during subsequent surgery. The adherence of the polymeric film to the skin surface is so strong that the possibility of lifting of the drape during surgery is effectively removed. Additionally, the cyanoacrylate composition can be applied as a liquid/gel to the skin surface which permits formation of an adherent film over any skin contour including elbows, knees, hips, and the like.

Since the polymeric film is naturally shed from the skin surface 1–4 days after application, there is no need to effect removal of the drape after surgery or to cause the skin trauma potentially associated with drape removal. This polymeric film forms a bacteriostatic or bactericidal barrier to external sources of wound contamination. Moreover, in a preferred embodiment, the cyanoacrylate composition is formulated to contain an antimicrobial agent which, over time, will be released from the resulting film thereby providing for peri and post-surgical infection protection not now available from conventional drapes.

Accordingly, in one of its method aspects, this invention is directed to a method for forming an adherent, surface conforming peripheral drape at a surgical site of a patient which method comprises:

(a) defining a surgical site on the patient;

(b) applying a sufficient amount of a composition comprising a polymerizable cyanoacrylate ester onto the skin surface of the patient peripheral to the surgical site defined in (a) above so as to peripherally surround this site with the composition;

(c) polymerizing the cyanoacrylate ester so as to form a flexible, waterproof, adhesive polymer layer which adheres to the area(s) where the adhesive was applied; and (d) conducting surgery on the patient at the surgical site defined in (a) above.

Preferably, the polymerizable cyanoacrylate ester comprises a cyanoacrylate ester which, in monomeric form, is represented by formula I:

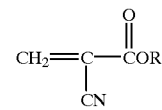

where R is selected from the group consisting of:
  alkyl of 1 to 10 carbon atoms,
  alkenyl of 2 to 10 carbon atoms,
  cycloalkyl groups of from 5 to 8 carbon atoms,
  phenyl,
  2-ethoxyethyl,
  3-methoxybutyl,
  and a substituent of the formula:

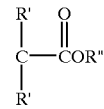

wherein each
  R' is independently selected from the group consisting of:
    hydrogen and methyl, and
  R" is selected from the group consisting of:
    alkyl of from 1 to 6 carbon atoms,
    alkenyl of from 2 to 6 carbon atoms,
    alkynyl of from 2 to 6 carbon atoms,
    cycloalkyl of from 3 to 8 carbon atoms,
    aralkyl selected from the group consisting of benzyl, methylbenzyl and phenylethyl,
    phenyl, and
    phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and more preferably alkyl of from 4 to 10 carbon atoms. Even more preferably, R is butyl, octyl, decyl or mixtures thereof and most preferably, R is n-butyl.

Application of the layer of cyanoacrylate composition is preferably made onto the surface of intact or uninjured skin and the incision is made subsequent to formation of the cyanoacrylate polymer layer. More preferably, the skin is further characterized as lacking any infection, open wounds, etc. which would permit the polymer to penetrate from the surface of the epidermis to or beyond the dermal layer. However, the location of the cyanoacrylate composition may be peripheral to and surround an infection or open wound.

In another preferred embodiment, the polymerized cyanoacrylate composition has a thickness of no more than about 1 millimeter and, more preferably, the polymer layer has a thickness of from about 2 to about 500 microns and still more preferably from about 20 to about 100 microns.

DETAILED DESCRIPTION OF THE PREFERRED EMBODIMENTS

This invention is directed to methods for draping a surgical site prior to surgery. However, prior to discussing this invention in further detail, the following terms will first be defined.

Definitions

As used herein, the following terms have the following meanings:

The term "surgical site" refers to the skin surface location at which surgery is to be conducted. The "surgical site" includes the intended site for surgical incision as well as wounds to the skin, such as puncture wounds by objects.

The term "incision" or "surgical incision" refers to any surgical penetration which extends beyond the epidermal or dermal layer of the patient's skin and includes, by way of example, incisions or punctures made by needles, knives (including surgical knives and surgical cautery knives), medical lasers, trocars, IV punctures, blood transfusion/ donation punctures, vaccine inoculation punctures, medicament punctures (e.g. insulin injections), punctures associated with hemodialysis, etc.

The term "wound" refers to any wound or injury, including surgically created wounds and accidental or traumatic wounds, such as compound fractures, gunshot wounds, knife wounds, pellet wounds, contaminated or infected wounds.

The term "peripheral to the surgical site" or "peripheral to the wound" refers to the area adjacent to the surgical site or the wound. This area typically extends from immediately adjacent the surgical site or wound up to about 30 cm and preferably from about 3 cm to about 30 cm from the surgical site. It being understood that the inner boundary of the area peripheral to the surgical site may conform to or parallel the shape of the surgical site, particularly if the surgical site is a wound.

The term "peripheral drape" or "fenestrated drape" refers to a drape formed by the application of a cyanoacrylate composition onto a patient's skin to form a drape around a surgical site such that the polymerized drape contains a region within the drape and over the surgical site which region is not covered by the polymerized cyanoacrylate composition.

The term "polymerizable cyanoacrylate esters" refers to polymerizable formulations comprising cyanoacrylate monomers or polymerizable oligomers which, in their monomeric form, are preferably compounds represented by formula I as described above.

More preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, octyl or decyl and most preferably, R is n-butyl. Mixtures of such compounds can also be employed.

A preferred cyanoacrylate ester for use in the invention is n-butyl-2-cyanoacrylate.

The polymerizable cyanoacrylate esters described herein rapidly polymerize in the presence of water vapor or tissue protein, and the cyanoacrylate bonds to human skin tissue without causing histotoxicity or cytotoxicity.

Such polymerizable cyanoacrylate esters are sometimes referred to herein as prepolymers and composition formulations comprising such esters are sometimes referred to herein as prepolymer compositions.

These polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (~20 weight percent or less), acetyl trihexyl citrate (~20 weight percent or less) butyl benzyl phthalate, dibutyl phthalate, dioctylphthalate, n-butyryl tri-n-hexyl citrate, diethylene glycol dibenzoate (~20 weight percent or less) and the like. The particular biocompatible plasticizer employed is not critical and preferred plasticizers include dioctylphthalate, and $C_2$–$C_4$-acyl tri-n-alkyl ($C_1$–$C_6$) citrates.

The term "polymerization inhibitor" refers to any material which is soluble or dispersible in the cyanoacrylate composition and which, in the amounts employed, inhibits the premature polymerization of the composition and is compatible with the skin. Suitable polymerization inhibitors are well known in the art and include 4-methoxyphenol (50 to 1000 ppm based on weight of composition absent any antimicrobial agent) and sulfur dioxide (50 to 1000 ppm based on weight of composition absent any antimicrobial agent). Other preferred polymerization inhibitors include glacial acetic acid, free radical inhibitors (e.g. hydroquinones) and the like which can be used alone or in combination with 4-methoxyphenol and/or $SO_2$.

The term "antimicrobial agent" refers to an agent which destroys microbes (i.e., bacteria, fungi, yeasts and viruses) thereby preventing their development and their pathogenic action. Preferably the antimicrobial agent is a complex of iodine molecules with a biocompatible polymer, more preferably the antimicrobial agent is polyvinylpyrrolidinone polymer completed with iodine.

Methods

The methods of this invention comprise the in situ formation of a cyanoacrylate polymer film on the skin surface peripheral to the surgical site or wound which polymer film acts as a peripheral or fenestrated surgical drape.

The surgical protocol preferably involves skin preparation prior to in situ formation of the cyanoacrylate polymer drape peripheral to the surgical site. Specifically, an antimicrobial agent is applied to the cleaned surgical site and the area peripheral to the surgical site. The antimicrobial agent can be any suitable agent including iodine based solutions, alcohols, etc. In one embodiment, an iodine prep solution is first applied to the surgical site and area peripheral to the surgical site. The patient's skin is then cleansed and scrubbed with this solution and subsequently washed off. Afterwards, an alcohol solution or a povidone iodine solution is applied to the surgical site and the area peripheral thereto to complete the skin preparation.

The surgical site and the area peripheral thereto is preferably dried and then an adherent polymeric drape is formed peripheral to this site by applying a cyanoacrylate ester composition to the intact skin surface peripheral to the surgical site. As noted above, this composition comprises polymerizable cyanoacrylate monomers and/or reactive oligomers which, upon contact with the surface skin moisture, tissue protein, etc. polymerizes in situ to form a cyanoacrylate polymer film.

Polymerization occurs at ambient skin temperature while maintaining the skin surface under suitable conditions to allow polymerization to proceed. In general, the particular length of time required for polymerization will vary depending on factors such as the amount of composition applied, the temperature of the skin, the moisture content of the skin, the surface area of skin to which the adhesive was applied, and the like. However, in a preferred embodiment, polymerization is generally complete within about 10 to about 60 seconds while the skin is maintained at ambient conditions. During this period, the patient is maintained in a position which permits the cyanoacrylate to polymerize and form a polymeric peripheral drape while minimizing any patient movement which might dislodge the cyanoacrylate peripheral to the surgical site or create undesirable bonding.

Sufficient amounts of the adhesive composition are employed to cover (i.e., coat) the area peripheral to the surgical site with a layer of the cyanoacrylate polymer. If necessary, excess cyanoacrylate monomer can be removed from the skin with a wipe or tissue paper before polymerization or, after polymerization, any polymer formed at unintended sites can be removed with acetone (nail polish remover).

It is contemplated that a peripheral drape of the present invention could be formed by the application of the cyanoacrylate polymer to the entire surgical site where the surgical site is intact skin and then the removal of the cyanoacrylate polymer from the skin at the surgical site with a wipe or tissue paper before polymerization, or after polymerization with acetone.

After polymerization, the resulting polymeric film forms a surgical incise drape which strongly adheres to the skin, is flexible and waterproof. Such strong adherence effectively eliminates the possibility that the drape will separate from the patient's skin during surgery. However, notwithstanding such strong adherence, the polymeric film defining the drape will only adhere to the skin for a period of about 1–4 days after which time it sloughs off. This occurs because the cyanoacrylate polymer adheres only to the uppermost portion of the epidermal layer which is continuously in the process of being sloughed off and replaced by the underlying cells. Accordingly, the cyanoacrylate drape need not be removed in the manner of conventional drapes attached through an adhesive layer whose removal can result in skin trauma.

The polymeric drape should be maintained in a unbroken manner surrounding and peripheral to the surgical site. This can be assured by careful application of the cyanoacrylate adhesive onto the skin. Additionally, the use of a plasticizer in the composition will facilitate the maintenance of the polymeric drape in an unbroken manner and will inhibit cracking of the drape.

In one preferred embodiment, after application of the initial polymeric layer, a second, preferably thinner, layer is applied thereto. Additional amounts of cyanoacrylate adhesive composition can be applied as needed to maintain an unbroken coating over the surface skin areas.

Application is conducted under conditions wherein the polymeric drape has a thickness of no more than about 1 millimeter and, more preferably, the polymer layer has a thickness of from about 2 to about 500 microns and still more preferably from about 20 to about 100 microns. If thinner polymeric drapes are desired, then the polymeric drape should have a thickness of from about 2 to about 50 microns and preferably from 10 to 40 microns. One drop of the cyanoacrylate composition can cover from about 6 cm$^2$ to about 25 cm$^2$ area. The amount of cyanoacrylate composition applied to a unit area of skin to obtain such thicknesses is well within the skill of the art.

After polymerization, the cyanoacrylate drape has biostatic properties. The peripheral cyanoacrylate surgical drape, by strongly adhering to the skin, impedes or prevents the migration of bacteria and other microbes from the area peripheral to the incision site into the incision. In one particularly preferred embodiment, the cyanoacrylate composition further comprises a compatible antimicrobial agent to provide antimicrobial properties to the composition.

Once the polymeric surgical incise drape is formed around and peripheral to the surgical site, the surgical site can then optionally be overdraped with sterile towels and sheets. In this optional embodiment, such towels and sheets are laid over (i.e., overdrape) the surgical site to define a limited field of the surgical site in which the actual incision is to be made and the subsequent operation is to be conducted. It is understood that the sterile towels and sheets may be around the surgical site prior to application of the cyanoacrylate composition adjacent to the surgical site.

A surgical incision may then be made at the surgical site. Any conventional incision can be made including those created by needles, knives (including surgical knives and surgical cautery knives), lasers, trocars, and the like. The incision may be a blunt incision. The particular incision made is not critical and is, of course, made relative to the surgery to be conducted. Where the surgical site is a wound, there may be no incision made prior to surgery.

The surgery is conducted using conventional methods and, upon completion of the surgery, the surgical wound is closed by conventional methods. In one embodiment, however, closure of the dermal layer of the surgical wound can be accomplished by contacting the skin sections, applying cyanoacrylate adhesive composition over the apposed skin sections and maintaining contact between these skin sections until the cyanoacrylate has polymerized. In a preferred embodiment, the cyanoacrylate composition is applied to the surface of the surgical site after the surgical site is closed to form a continuous polymerized cyanoacrylate drape which covers the surgical site and the area peripheral to the surgical site.

The size and thickness of the polymeric drape formed onto the skin surface area can be readily controlled by the amount and viscosity of cyanoacrylate ester composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate composition and the like.

In applicators, the cyanoacrylate composition is stored at ambient conditions. The cyanoacrylate composition may be provided as a sterile solution or may be sterilized as needed.

Because the cyanoacrylate polymer layer is waterproof, the patient is not prevented from bathing or being bathed and other activities involving exposure to water during the period the polymer layer protects the surgical site provided a further application of the cyanoacrylate composition is made over the surgical site after surgery.

Compositions

The cyanoacrylate compositions comprising the polymerizable cyanoacrylate esters are prepared by conventional methods of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin layer. Contrarily, where application is to be made to a specific position on the skin (e.g., elbow surfaces), higher viscosity compositions, including those containing thiotropic materials, are preferred to prevent "running" of the material to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate adhesive is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239[8] and 4,038,345[13] both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate adhesive compositions preferably include a biocompatible plasticizer and such plasticizers are preferably included in the composition at from about 10 to 30 weight percent and more preferably at from about 18 to 25 weight percent based on the total weight of the composition absent any antimicrobial agent.

Additionally, the cyanoacrylate compositions described herein preferably include a polymerization inhibitor in an effective amount to inhibit premature polymerization of the composition. In one embodiment the inhibitor is sulfur dioxide which is employed at from about 50 to 1000 ppm, preferably from 100 to 500 ppm, based on the total weight of the composition absent any antimicrobial agent. In another embodiment the inhibitor is 4-methoxyphenol which is employed at from about 50 to 500 ppm, preferably from 100 to 500 ppm, based on the total weight of the composition absent any antimicrobial agent. In a particularly preferred embodiment where the cyanoacrylate composition additionally comprises povidone-iodine, this inhibitor is 4-methoxyphenol which is employed at from about 50 to 500 ppm based on the total weight of the composition absent any antimicrobial agent.

The polymerizable cyanoacrylate ester compositions may additionally contain one or more optional additives such as colorants, perfumes, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernible color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935[18], which patent is incorporated herein by reference in its entirety.

In a particularly preferred embodiment, the cyanoacrylate ester composition further comprises an antimicrobially effective amount of a compatible antimicrobial agent. Such compositions preferably comprise from about 1 to about 40 and preferably 5 to 30 weight percent of the compatible antimicrobial agent either as a solution or as a suspension based on the total weight of the composition. Compatible antimicrobial agents are those which are either soluble or suspendable in the cyanoacrylate composition, which do not cause premature polymerization or prevent polymerization of the cyanoacrylate composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidinone polymer which, when complexed with iodine, is also referred to under the common name of povidone-iodine available from BASF, Mt. Olive, N.J., USA. When povidone-iodine is employed in the cyanoacrylate composition, it is preferably from about 5 to about 40 weight percent and more preferably from about 10 to 25 weight percent is added to the cyanoacrylate composition based on the total weight of the composition.

Cyanoacrylate compositions comprising, for example, povidone-iodine are described by Greff, et al., U.S. Pat. No. 5,684,042[19] which application is incorporated herein by reference in its entirety.

Other suitable antimicrobial agents include complexes of iodine molecules with copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like. Preferably, however, the iodine containing polymer is povidone iodine which is commercially available from a number of sources.

The use of a compatible antimicrobial agent in the composition permits the agent to be released from the polymeric drape thereby reducing microbial growth under the drape during surgery. Additionally, the compatible antimicrobial agent in the composition migrates from the drape toward the incision site, thereby reducing microbial contamination at the incision site. Since the drape is maintained peripheral to the surgical site for 1–4 days after surgery, the release of antimicrobial agent further provides post-surgical anti-infection benefits.

Utility

The methods described herein are useful in forming a polymeric surgical incise drape peripheral to and surrounding the surgical site of a mammalian patient. The polymeric drape finds particular utility in inhibiting microbial contamination of the incision during surgeries conducted on such patients. Such mammalian patients preferably include humans as well as domestic animals such as horses, cows, dogs, sheep, cats, etc. The maintenance of the polymeric film peripheral to the surgical incision after completion of the surgery is expected to reduce the incidence of infection by inhibiting microbial contamination of the incision.

The following examples illustrates certain embodiments of the invention but is not meant to limit the scope of the claims in any way.

In the examples below, all temperatures are in degrees celsius (unless otherwise indicated) and all percents are weight percent (also unless otherwise indicated) except for percent inhibition which is true mathematical percentage. Additionally, the following abbreviations have the following meanings. If an abbreviation is not defined, it has its generally accepted meaning.

CFU = colony forming units
ml = milliliters
mm = millimeters
ppm = parts per million
PVP-$I_2$ = polyvinylpyrrolidone iodine complex
SAB-DEX = Sabouraud Dextrose
TSA = trypticase soy agar

EXAMPLE 1

The following example was conducted to ascertain the antimicrobial effect of a cyanoacrylate polymer film comprising PVP-iodine.

A. Preparation of the Inoculum

Specifically, the surfaces of two TSA plates, 100×15 mm, were inoculated with stock cultures (maintained on TSA slants) with the following microorganisms using a sterile inoculating loop: *Staphylococcus aureus* (ATCC No. 6538) and *Staphylococcus epidermidis* (ATCC No. 12228). The plates were incubated at 30° to 35° C. for 24 hours. The surfaces of two SAB-DEX agar plates were streaked with *Candida albicans* and incubated at 20–25° C. for 48 hours.

The cultures were harvested with sterile saline. Each culture suspension was collected in a sterile container and sufficient sterile saline was added to reduce the microbial count to obtain a working suspension of approximately 1×10$^8$ CFU's per mL.

The specific microorganisms recited above were selected for inclusion herein because they are common human skin pathogens (bacteria and fungus).

B. Inoculation of Plates

Each of the three test microorganisms was used to inoculate individual TSA plates by streaking them with sterile cotton tip applicators saturated with the appropriate suspension. The plates were allowed to dry.

C. Inhbition Study

Films of polymerized n-butyl cyanoacrylate comprising 0%, 10%, 15%, 20% or 30% iodine polyvinylpyrrolidone complex were formed on 25 mm glass fiber filter disks by addition of the corresponding prepolymerized cyanoacrylate composition to the disks and subsequent polymerization in situ. The films were then cut into approximately 11 to 13 mm$^2$ pieces. The pieces were placed in the center of the appropriate inoculated TSA plates. An untreated filter disk was cut into half, and one-half was placed in the center of the appropriate inoculated TSA plate and the other one-half was place in the center of non-inoculated TSA plates, to serve as a negative control. Two inoculated plates of each microorganism were also used as positive controls without the test article. These plates were then incubated for 3 days at 30° to 35° C. After incubation, the plates were removed and examined for any signs of microbial growth inhibition.

The results of this analysis are set forth in Tables I–III below. The sample sizes reported are the portion of the sample actually in contact with the agar. The sizes of the zone of inhibition include the diameters of the entire zone including the test article size.

TABLE I

Results for *Staphylococcus aureus*

| SAMPLE:<br>n-butyl cyanoacrylate<br>comprising | SAMPLE SIZE[1]<br>(in mm) | ZONE OF<br>INHIBITION[1]<br>(in mm) |
|---|---|---|
| 0% PVP-$I_2$ | 12 | 12 |
| 10% PVP-$I_2$ | 12 | 15 |
| 15% PVP-$I_2$ | 12.5 | 14 |
| 20% PVP-$I_2$ | 11.5 | 15.5 |
| 30% PVP-$I_2$ | 12.5 | 20 |
| Untreated Filter Disk | 13[2] | 13[2] |
| Negative Control | 13[2] | 13[2] |
| Positive Control | n/a | 0 |

TABLE II

Results for *Staphylococcus epidermis*

| SAMPLE:<br>n-butyl cyanoacrylate<br>comprising | SAMPLE SIZE[1]<br>(in mm) | ZONE OF<br>INHIBITION[1]<br>(in mm) |
|---|---|---|
| 0% PVP-$I_2$ | 12 | 12 |
| 10% PVP-$I_2$ | 12.5 | 15 |
| 15% PVP-$I_2$ | 12 | 15.5 |
| 20% PVP-$I_2$ | 12.5 | 20.5 |
| 30% PVP-$I_2$ | 13 | 27.5 |
| Untreated Filter Disk | 13[2] | 13[2] |
| Negative Control | 13[2] | 13[2] |
| Positive Control | n/a | 0 |

TABLE III

Results for *Candida albicans*

| SAMPLE:<br>n-butyl cyanoacrylate<br>comprising | SAMPLE SIZE[1]<br>(in mm) | ZONE OF<br>INHIBITION[1]<br>(in mm) |
|---|---|---|
| 0% PVP-$I_2$ | 12 | 12 |
| 10% PVP-$I_2$ | 12.5 | 18.5 |
| 15% PVP-$I_2$ | 12.5 | 23 |
| 20% PVP-$I_2$ | 12.5 | 20.5 |
| 30% PVP-$I_2$ | 13 | 29.5 |
| Untreated Filter Disk | 13[2] | 13[2] |
| Negative Control | 13[2] | 13[2] |
| Positive Control | n/a | 0 |

[1]average of two runs
[2]single run only

The above data demonstrates that the compositions of this invention produce a polymeric cyanoacrylate film which have broad spectrum of antimicrobial activity. Based on these results, it is expected that these compositions would be antimicrobial when formed in situ on mammalian skin surfaces.

EXAMPLE 2

This example illustrates how a surgical incise drape formed in the manner of this invention could be used during surgery. In this example, an abdominal surgical incision is to be made on an adult male undergoing a second percutaneous nephrolithotomy or kidney stone removal from the left kidney.

Specifically, an adult human male (age 50) is scheduled for surgery. The patient previously had kidney stones removed from the left kidney. The patient (after thorough skin cleaning) is placed and secured on an operating table and anesthetized. Shaving of the surgical incision area can optionally be performed if such is deemed necessary by the attending surgeon. The patient then undergoes a five minute back scrub using cleansing pads and an iodine based cleansing solution such as ethanolic povidone-iodine. After the surgical scrub, the back is thoroughly rinsed with sterile distilled water. An antimicrobial solution of iodine is then applied to the same area and allowed to dry.

At this time, an antimicrobial cyanoacrylate composition comprising 63% by weight butyl cyanoacrylate, 17% by weight acetyl tri-n-butyl citrate, 20% povidone iodine; 250 parts per million of 4-methoxyphenol and 100 parts per million sulfur dioxide (each based on the total weight of the composition) is applied to the periphery of the original surgical scar over an area of approximately 25 centimeters by 50 centimeters forming a clear area or window over the proposed incision site which site will be located in the center of this window. The composition is allowed to thoroughly cure (~100 seconds) whereupon a durable and flexible surgical incise drape is formed over the applied area. This area is then draped with standard sterile surgical drapes made of a waterproof paper material to create a surgical field within the surgical incise drape. The surgical field defines an area of approximately 8 centimeters by 1 centimeter at approximately the center of the surgical incise drape. Surgery is performed. Afterwards, the paravertebral muscle and the fascia layers are closed with standard absorbable surgical sutures. The skin is then closed with a standard running skin suture.

At this time, the sterile surgical drapes made of a waterproof paper material are removed from the patient leaving only the surgical incise drape which is strongly adherent to the skin. A surgical dressing is applied over the incision site and the patient is awakened from the anesthetic agent. The surgical dressing is checked every 4 hours for signs of seepage and changed daily until patient is discharged (typically 2–5 days after surgery).

The surgical incise drape formed by the film of cyanoacrylate polymer sloughs off naturally over 1–4 days after surgery as the patient's outer layer of skin naturally sloughs off without any complications.

EXAMPLE 3

This example illustrates how a surgical incise drape formed in the manner of this invention could be used during surgery to close a knife wound to the right thigh.

Specifically, an adult female (age 24) diagnosed with a puncture wound is scheduled for outpatient surgery to repair the wound. The patient, after thorough skin cleansing, is placed and secured on an operating table, and the right thigh is anesthetized (local anesthesia). The patient then undergoes a five minute scrub of the right thigh using cleansing pads and an iodine based cleansing solution such as ethanolic povidone-iodine. After the surgical scrub, the right thigh is thoroughly rinsed with sterile distilled water. An antimicrobial solution of iodine is then applied to the same area and allowed to dry.

At this time, a viscous antimicrobial cyanoacrylate composition comprising 58% by weight butyl cyanoacrylate, 5% by weight polymethyl methacrylate, 17% by weight acetyl tri-n-butyl citrate, 20% povidone iodine, 100 parts per million glacial acetic acid; 250 parts per million 4-methoxyphenol and 100 parts per million sulfur dioxide (each based on the total weight of the composition) is applied peripherally to the wound area. The composition is applied as a band about 5 cm wide and about 1 cm away from the wound. The composition is allowed to thoroughly cure (~100 seconds) whereupon a coherent, durable and flexible surgical incise drape is formed over the applied area. This area is then draped with standard sterile surgical drapes made of a waterproof paper material to create a surgical field within the surgical incise drape. Surgery is performed to repair the knife wound. Afterwards, the muscle and the fascia layers are closed with standard absorbable surgical sutures. Afterwards, the skin is closed by the application of a cyanoacrylate composition specifically designed for skin closure which may be different from that defined above (e.g., without plasticizer). A layer of the cyanoacrylate composition set forth above (with plasticizer) may also be placed over the surgical site. The cyanoacrylate polymer film naturally sloughs off within 1–4 days after formation. The povidone-iodine in the film renders the film antimicrobial thereby providing an antimicrobial effect during this period.

From the foregoing description, various modifications and changes in the composition and method will occur to those skilled in the art. All such modifications coming within the scope of the appended claims are intended to be included therein.

What is claimed is:

1. A method for forming an adherent, surface conforming drape peripheral to a surgical site of a patient which method comprises:

(a) defining a surgical site on the patient;
   (b) applying a sufficient amount of a cyanoacrylate composition comprising polymerizable cyanoacrylate ester monomers and/or oligomers to the skin surface of the patient peripheral to the surgical site defined in (a) above;
   (c) polymerizing the cyanoacrylate ester so as to form a flexible, waterproof, adhesive polymer layer which adheres to the area(s) where the composition was applied; and
   (d) conducting surgery on the patient at the surgical site defined in (a) above.

2. The method according to claim 1 wherein the polymerizable cyanoacrylate composition comprises a cyanoacrylate ester which, in monomeric form, is represented by formula I:

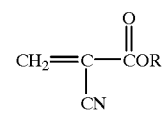

where R is selected from the group consisting of:
  alkyl of 1 to 10 carbon atoms,
  alkenyl of 2 to 10 carbon atoms,
  cycloalkyl groups of from 5 to 8 carbon atoms, phenyl,
2-ethoxyethyl,
3-methoxybutyl,
and a substituent of the formula:

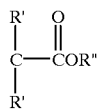

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alknyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 2 to 10 carbon atoms.

4. The method according to claim 3 wherein R is alkyl of from 4 to 10 carbon atoms.

5. The method according to claim 4 wherein R is selected from the group consisting of butyl, octyl or decyl.

6. The method according to claim 5 wherein R is n-butyl.

7. The method according to claim 1 wherein said cyanoacrylate composition further comprises an antimicrobially effective amount of a compatible antimicrobial agent.

8. The method according to claim 7 wherein the compatible antimicrobial agent is polyvinylpyrrolidone iodine.

9. The method according to claim 1 wherein said cyanoacrylate composition further comprises a biocompatible plasticizer.

10. The method according to claim 9 wherein said biocompatible plasticizer is dioctyl phthalate.

11. The method according to claim 1 wherein said cyanoacrylate composition further comprises a polymerization inhibitor.

12. The method according to claim 11 wherein said polymerization inhibitor is sulfur dioxide.

13. The method according to claim 1 wherein the polymer layer has a thickness of no more than about 1 millimeter.

14. The method according to claim 1 which further comprises closing the dermal layer of the surgical incision with a polymerizable cyanoacrylate composition described in claim 1.

15. A method for forming an adherent, surface conforming surgical incise drape peripheral to a surgical site of a patient which method comprises:

(a) defining a surgical site on the patient;

(b) applying a sufficient amount of a polymerizable cyanoacrylate composition comprising polymerizable cyanoacrylate ester monomers and/or oligomers onto the skin surface peripheral to the surgical site defined in (a) above wherein the polymerizable cyanoacrylate ester, in monomeric form, comprises:

(i) polymerizable n-butyl cyanoacrylate which, in monomeric form, is represented by formula II:

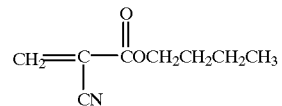

(ii) from 18 to 25 weight percent of dioctylphthalate based on the total weight of the composition absent polyvinylpyrrolidone iodine;

(iii) from 5 to 40 weight percent of polyvinylpyrrolidone iodine based on the total weight of the composition;

(c) polymerizing the cyanoacrylate composition thereby forming a flexible, waterproof, adhesive polymer layer which adheres to the area(s) where the composition was applied; and (d) conducting surgery on the patient at the surgical site defined in (a) above.

16. The method according to claim 15 wherein the polymer layer has a thickness of no more than about 1 millimeter.

* * * * *